(12) United States Patent  
Shu et al.

(10) Patent No.: US 9,414,909 B1  
(45) Date of Patent: Aug. 16, 2016

(54) GENTLE ARTIFICIAL HEART VALVE WITH IMPROVED WEAR CHARACTERISTICS

(71) Applicant: PATENTSPLUS LLC, North Tustin, CA (US)

(72) Inventors: Stephen K. Shu, Irvine, CA (US); Benton Bejach, North Tustin, CA (US)

(73) Assignee: PatentsPlus LLC, North Tustin, CA (US)

( * ) Notice: Subject to any disclaimer, the term of this patent is extended or adjusted under 35 U.S.C. 154(b) by 0 days.

(21) Appl. No.: 14/603,101

(22) Filed: Jan. 22, 2015

(51) Int. Cl.  
*A61F 2/24* (2006.01)

(52) U.S. Cl.  
CPC ............. *A61F 2/24* (2013.01); *A61F 2/2421* (2013.01)

(58) Field of Classification Search  
CPC ........ A61F 2/2421; A61F 2/2424; A61F 2/24  
See application file for complete search history.

(56) References Cited

U.S. PATENT DOCUMENTS

| | | | |
|---|---|---|---|
| 1,737,710 A | 6/1927 | Erbach | |
| 3,613,677 A | 10/1971 | Blasko | |
| 4,375,941 A | 3/1983 | Child | |
| 4,611,578 A | 9/1986 | Heimes | |
| 4,648,877 A | 3/1987 | Lundback | |
| 4,786,240 A | 11/1988 | Koroly et al. | |
| 5,241,986 A * | 9/1993 | Yie | B05B 1/306 137/512 |
| 5,411,552 A | 5/1995 | Andersen et al. | |
| 5,758,666 A | 6/1998 | Larson, Jr. et al. | |
| 5,766,207 A | 6/1998 | Potter et al. | |
| 7,575,594 B2 | 8/2009 | Sieracki | |
| RE41,394 E | 6/2010 | Bugge et al. | |
| 8,021,422 B2 | 9/2011 | Tinker | |
| 2010/0057046 A1 | 3/2010 | Stevens et al. | |
| 2011/0144744 A1 | 6/2011 | Wampler | |
| 2013/0041460 A1 | 2/2013 | Heilman et al. | |

* cited by examiner

*Primary Examiner* — David Isabella  
*Assistant Examiner* — Suba Ganesan  
(74) *Attorney, Agent, or Firm* — Knobbe, Martens, Olson & Bear, LLP

(57) ABSTRACT

Disclosed herein is an artificial heart valve, comprising a valve housing comprising a distal plate and a proximal valve ring operably connected by a plurality of struts; one or more helical springs having a proximal end and a distal end; and a bellows spring having a proximal end, enclosed area, and a distal end, the distal end of the bellows spring operably attached to a first surface of a moving spring plate positioned axially in between the one or more helical springs and the bellows spring, the proximal end of the helical spring operably attached to a second surface of the moving spring plate; and a movable valve plate operably attached to the proximal end of the bellows spring, wherein the movable valve plate is configured to reversibly contact the proximal valve ring to create a seal and close the valve.

22 Claims, 5 Drawing Sheets

FIG. 4 VALVE FLOW AND PRESSURE

GENTLE ARTIFICIAL HEART VALVE WITH IMPROVED WEAR CHARACTERISTICS

BACKGROUND

Field of the Invention

The invention generally relates to an artificial heart valve, components of an artificial heart valve, and methods of using the same.

SUMMARY

Disclosed herein are artificial heart valves, which can in some cases include a moveable valve ring that moves to a flat gate plate to form a seal valve. The valve can also include a flat contact area between the moveable valve ring and the valve plate, to minimize the force per unit area of contact between the moveable valve ring and the valve plate. The valve can also include a bellows spring operably attached to the moveable valve ring. The bellows spring can be operably hung to a helical spring assembly. In some cases, an end of the helical spring assembly is operably attached to a cage housing, to provide a force reference point. The bellows spring can have a first spring constant and the helical spring assembly can have a second spring constant, the first spring constant and the second spring constant configured to assist in opening and closing of the valve, minimizing pressure and keeping movement gentle. In some embodiments, the bellows spring and the helical spring assembly are configured to isolate pressure on the valve, and substantially prevent high pressure forces from acting on the valve. The bellows spring can be suspended on the helical spring assembly, reducing the pressure on the valve. The valve can be configured such that the valve gate force is effected substantially only by an area of the moveable valve ring that contacts the flat gate plate to seal the valve, minimizing the effect of blood pressure on valve pressure.

In some embodiments, the moveable valve ring is configured to not move radially or slide to lengthen the lifespan of the valve. The valve can be configured such that the impact force upon closure of the valve is minimized, and movement of the bellows spring and the helical spring assembly are programmed to control the valve. The valve can comprise a metal, plastic, or other biocompatible material.

In some embodiments, disclosed herein is an artificial heart valve that can include a movable valve plate configured to reversibly contact a proximal valve ring to create a seal and close the valve. In some cases, at least some stress forces on the valve can be alleviated via at least one helical spring operably attached to a bellows spring, the bellows spring operably attached to the movable valve plate. In some embodiments, the bellows spring has a pre-selected spring constant sufficient that the movable valve plate contacts the proximal valve ring substantially entirely by virtue of the spring force of the bellows spring, reducing the impact force on the valve. In some embodiments, the bellows spring has a pre-selected spring constant sufficient to prevent a sudden stop force on the movable valve plate or the proximal valve ring. The proximal valve ring can have a first surface having a surface area and the movable valve plate can have a second surface having a surface area, and less than the entire surface area of the first surface and the second surface reversibly contact each other to create the seal to close the valve in order to reduce the pressure force on the valve.

In some embodiments, the artificial heart valve can be configured to reduce hemolysis of red blood cells flowing through the valve by virtue of at least the large contact area and low impact force on the valve. The valve can also be configured such that no valve component is configured to move in a direction other than coaxial with respect to the longitudinal axis of the valve. The valve can be configured to have a long life expectancy within a patient of, for example, at least 25 years.

In some embodiments, disclosed herein is an artificial heart valve that includes a valve housing comprising a distal plate and a proximal valve ring operably connected by a plurality of struts; one or more helical springs having a proximal end and a distal end; and a bellows spring having a proximal end, enclosed area, and a distal end, the distal end of the bellows spring operably attached to a first surface of a moving spring plate positioned axially in between the one or more helical springs and the bellows spring, the proximal end of the helical spring operably attached to a second surface of the moving spring plate; and a movable valve plate operably attached to the proximal end of the bellows spring, wherein the movable valve plate is configured to reversibly contact the proximal valve ring to create a seal and close the valve. The valve can include a plurality of intertwined helical springs. In some embodiments, one or more of the helical springs, bellows spring, movable valve plate, and the movable spring plate are configured for axial movement with respect to the valve housing, but not radial movement with respect to the valve housing. One or more of the helical springs can be linear or nonlinear. One or more of the helical springs can have a first spring constant and the bellows spring can have a second spring constant, wherein the first spring constant is greater than the second spring constant. The first spring constant can be, for example, at least about 25%, 50%, or more greater than the second spring constant. The valve can be partially or completely made of a biocompatible titanium or an alloy thereof.

DETAILED DESCRIPTION

The heart is the muscle that drives the cardiovascular system in living beings. Acting as a pump, the heart moves blood throughout the body to provide oxygen, nutrients, hormones, and to remove waste products. The blood follows two separate pathways in the human body, the so-called pulmonary and systemic circulatory circuits. In the pulmonary circuit, the heart pumps blood first to the lungs to release carbon dioxide and bind oxygen, and then back to the heart. Thus, oxygenated blood is constantly being supplied to the heart. In the systemic circuit, the longer of the two, the heart pumps oxygenated blood through the rest of the body to supply oxygen and remove carbon dioxide, the byproduct of metabolic functions carried out throughout the body. The heart supplies blood to the two circuits with pulses generated by the orderly muscular contraction of its walls.

Figure 1:
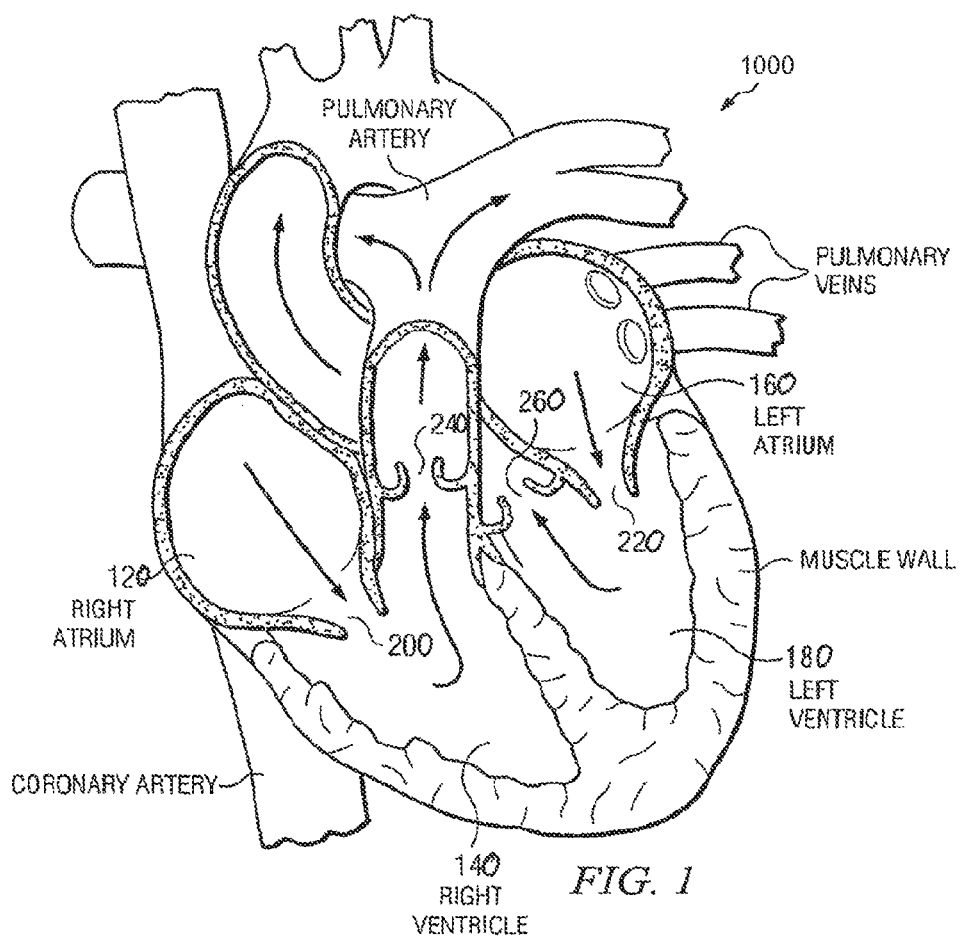
FIG. 1 is a representation of the human heart.

In order to keep blood moving through these two separate circulatory circuits, the human heart has four distinct chambers that work in pairs. As illustrated in FIG. 1, the heart 100 includes a right atrium 120, a right ventricle 140, a left atrium 160, and a left ventricle 180. One pair of chambers, the right ventricle and left atrium, is connected directly to the pulmonary circuit. In it, de-oxygenated blood from the body is pumped from the right ventricle 140 to the lungs, where it is oxygenated, and then back to the left atrium 160.

In the systemic circuit, the other pair of chambers pumps the oxygenated blood through body organs, tissues and bones. The blood moves from the left atrium 160, where it flows from the lungs, to the left ventricle 180, which in turn pumps the blood throughout the body and all the way back to the right atrium 120. The blood then moves to the right ventricle 140 where the cycle is repeated. In each circuit, the blood enters the heart through an atrium and leaves the heart through a ventricle.

Thus, the ventricles 140, 180 are essentially two separate pumps that work together to move the blood through the two circulatory circuits. Four check valves control the flow of blood within the heart and prevent flow in the wrong direction. A tricuspid valve 200 controls the blood flowing from the right atrium 120 into the right ventricle 140. Similarly, a bicuspid valve 220 controls the blood flowing from the left atrium 160 into the left ventricle 180. Two semilunar valves (pulmonary 240 and aortic 260) control the blood flow leaving the heart toward the pulmonary and systemic circuits, respectively. Thus, in each complete cycle, the blood is pumped by the right ventricle 140 through the pulmonary semilunar valve 240 to the lungs and back to the left atrium 160. The blood then flows through the bicuspid valve 220 to the left ventricle 180, which in turn pumps it through the aortic semilunar valve 260 throughout the body and back to the right atrium 120. Finally, the blood flows back to the right ventricle 140 through the tricuspid valve 200 and the cycle is repeated.

In some cases, valves in the circulatory system such as the tricuspid, mitral, aortic, or pulmonic valves heart valves are deficient or fail. The causes of partial or total heart valve failure include congenital/structural defects, disease and infection. However, the most common cause of valve failure is dilation of the valve annulus. This occurs as part of the generalized cardiac structural dilatation allied to cardiomyopathy and heart failure. The consequences of heart valve failure can vary depending on the seriousness of the failure, but in most cases the heart's efficiency and the efficiency of the circulatory system is seriously affected and complications often result.

Failure or insufficiency of the heart valves frequently results in mitral/tricuspid valve regurgitation. In the case of the mitral valve, regurgitation results in back pressure in the lungs, whereas tricuspid valve regurgitation can result in high back pressures in the venous circulation. Clearly, this is undesirable for the health of the heart, as well as for the lungs and other organs of the body. Valve failure can lead to ineffective and/or inefficient cardiac pumping, ventricular and atrial enlargement, pulmonary and/or circulatory hypertension, heart failure and in some cases, death.

Methods exist for repairing and replacing cardiac valves and other valves of the body are available. One form of treatment involves replacement of the entire valve. Artificial valves need to be configured to withstand the physiologic force of blood flow throughout the circulatory system, and the life expectancy of the artificial valve may oftentimes be less than that of the patient in which that valve is implanted, potentially necessitating another valve replacement.

In some embodiments, disclosed herein is an artificial heart valve with increased life expectancy and decreased wear resistance. The valve can include a housing, a first spring, and a second spring connected at an end to the first spring. The first spring can comprise one or more helical springs. The second spring can have a bellows configuration and be operably connected to the helical springs at a first end, the bellows spring having a spring constant that is less than that of the helical springs. The second spring can be operably connected to a movable valve plate at the second end of the second spring. A movable spring plate can be present between the first spring and the second spring. The housing can include a top plate and a bottom ring operably connected by one, two, or more struts. Components of the valve, such as the first spring, second spring, movable spring plate, and movable valve plate are configured to move in an axial direction parallel to the longitudinal axis of the valve, but not in a direction transverse to the longitudinal axis of the valve in some embodiments.

Figure 2:
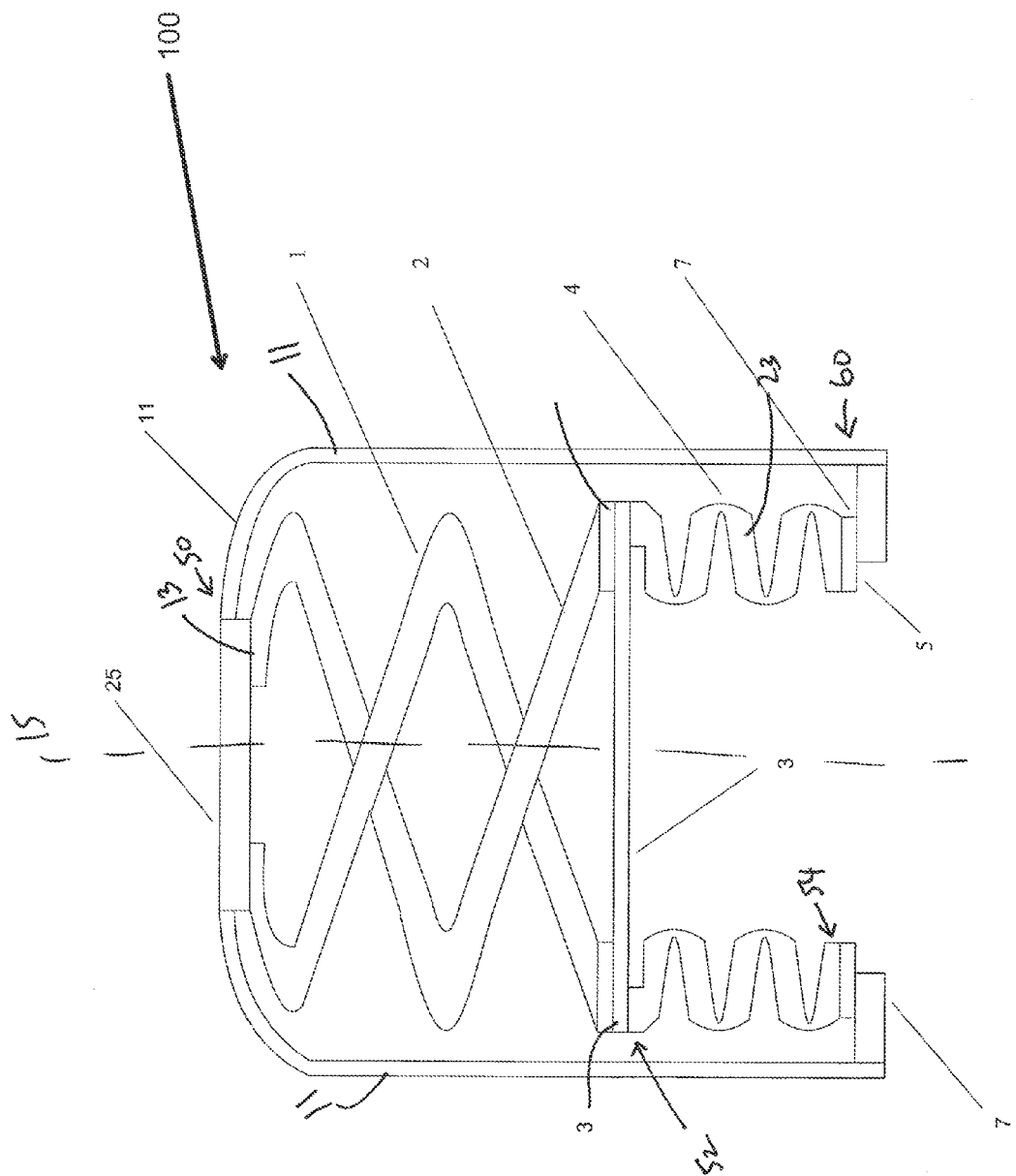
FIG. 2 illustrates a sectional schematic view of an artificial heart valve, according to some embodiments of the invention.

FIG. 2 illustrates a sectional view of an artificial heart valve 100 in a closed position, according to some embodiments of the invention. As illustrated schematically in FIG. 2, the valve 100 comprises a valve housing 10, such as a housing which can be made, for example, of a biocompatible material such as a metal or metallic alloy. In some embodiments, the housing 10 can take the form of a cage-like structure and can include a plurality (e.g., 2, 3, 4, 5, or more) of struts, such as generally axially oriented struts 11 operably connected to a fixed top plate 25 at a first end 50 and a fixed bottom valve plate 7 at a second end 60 as illustrated. The cage-like structure could have a generally cylindrical or another geometry. In some embodiments, the valve housing 10 can include and/or take the form of a self-expandable or balloon-expandable stent with a desired wall pattern depending on the desired clinical result. Within the valve housing 10 are one, two, or more springs 1, 2 that can be helical in configuration in some embodiments, as well as be operably intertwined as shown. The springs 1, 2, can be operably connected distally (also referred to as downstream relative to the direction of blood flow through the valve when the valve is implanted) at 13 to top plate 25 and proximally (also referred to as upstream relative to the direction of blood flow through the valve when the valve is implanted) at location 9 to a first surface of movable spring plate 3. The movable spring plate 3 could be generally flat, or arcuate similar to a jar lid in some embodiments. The distal end of a second spring 4 can be attached to a second surface of movable spring plate 3 opposite the first surface. The movable spring plate 3 can be configured to move in a substantially axial direction parallel to the longitudinal axis 15 of the valve 100, but has sufficient rigidity that it does not move in a direction substantially transverse or oblique to the longitudinal axis 15 of the valve 100 in some embodiments. The movable spring plate 3 can move axially in either an upstream or downstream direction along with axial movement of the springs 1, 2, and spring 4.

The helical springs 1, 2, can be operably connected to top plate 25 and movable spring plate 3 via welding, crimping, adhesives, or other techniques, or the components could be integrally formed and laser cut out of a tube in some embodiments. The top plate 25 and movable spring plate 3 can be, in some embodiments, relatively more rigid components in some embodiments with respect to the springs 1, 2.

In some embodiments, one, two, or more springs 4 can be axially spaced upstream apart from helical springs 1, 2 as illustrated in FIG. 2. Spring 4 can take the form of a bellows structure having a plurality of flexible folds 23. The bellows spring 4 can be operably connected at a first end 52, such as a downstream end to the movable spring plate 3, such as at a surface opposite the surface in which the helical springs 1, 2 connect to the movable spring plate 3. The bellows spring 4 can be operably connected at a second end 54, such as an upstream end to the movable valve plate 5. The movable valve plate 5 can move axially in either an upstream or downstream direction along with axial movement of bellows spring 4.

The movable valve plate 5 can releasably contact the fixed bottom valve plate 7 in order to create the valve seal. The fixed bottom valve plate 7 can in some embodiments take the form of an annular valve ring with an aperture 110 in which blood can flow therethrough when the valve 100 is in an open position; the valve 100 can assume a closed position when a surface of the movable valve plate 5 comes into contact with an opposing surface of the fixed valve ring 7, temporarily creating a seal in which blood is prevented from flowing therethrough. The opposing surfaces of the movable valve plate 5 and the fixed valve ring 7 can be heat treated, stress relieved, and/or ground micro flat in some embodiments. In contrast to conventional valves having a number, such as two, three, or more valve leaflets that coapt to provide the valve seal, some embodiments of the valve 100 lack any such leaflets, and the interaction of the movable valve plate 5-fixed valve ring 7 advantageously provides substantially less blood flow restriction and/or turbulence across the valve. In some embodiments, the valve contact area for closure can be arcuate, such as oval or circular in contrast to conventional leaflet designs. The valve also can be configured to create minimal resonance or resonant sounds for quiet operation.

The valve 100 can be attached at one, two, or more locations 22 along the fixed valve ring 7 to the native valve annulus via conventional techniques (e.g., suturing, anchors, adhesives, and the like), and/or be secured by radially outward forces of a stent housing, for example. In some embodiments, the fixed valve ring 7 can include anchoring portions with apertures in which sutures can be threaded therethrough to facilitate attachment of the artificial valve 100 to the native valve annulus or other desired location. In some embodiments, the fixed valve ring 7 can include barbed anchors or other anchoring mechanism to facilitate attachment of the artificial valve 100 to the native valve annulus or other desired location.

The valve 100 can be implanted via conventional surgical techniques, via minimally invasive techniques (such as via a transapical approach, for example), or percutaneously delivered within a delivery catheter in some embodiments.

The valve including some or all the components can be made of, for example, biocompatible titanium, stainless steel, other metal or metal alloys, or other biocompatible materials. The valve could be sized and configured as a replacement mitral valve, aortic valve, tricuspid valve, pulmonic valve, or a non-cardiac valve depending on the desired clinical result. In some embodiments, a 3D printer could be used to print the valve.

The valve 100 can function as follows in some embodiments. The valve 100 opens in some cases by force from blood pressure created from increased pressure in the cardiac chamber proximal to the valve (e.g., the left atrium for a replacement mitral valve; left ventricle for a replacement aortic valve; right atrium for a replacement tricuspid valve; and right ventricle for a replacement pulmonic valve) and the force from the helical springs 1, 2 can allow the movable valve plate 5 to release the seal formed with fixed bottom ring or plate 7, and bellows spring 4, valve plate 3, helical springs 1, 2, and top plate 25 will move axially in a distal (e.g., downstream) direction. As the blood pressure force declines the helical spring force predominates, allowing the valve to close. When the valve reaches a set position, e.g., a ⅔ open position in some embodiments, the helical spring force again equals the blood pressure, the moving spring plate 3 ceases moving, and the bellows 4 moves until the valve closes. The net force while closing the valve is relatively small, resulting in advantageously minimal force transmission to the bottom valve plate or ring 7. Pressure on the valve surface can in some cases be much smaller than conventional valves, thus reducing or preventing damage to red blood cells during valve closure.

A linear spring is one with a linear relationship between force and displacement, meaning the force and displacement are directly proportional to each other. A graph showing force vs. displacement for a linear spring will always be a straight line, with a constant slope.

A nonlinear spring has a nonlinear relationship between force and displacement. A graph showing force vs. displacement for a nonlinear spring will be more complicated than a straight line, with a changing slope. In some embodiments, the helical springs 1, 2 and the bellows spring 4 are nonlinear; although linear springs for either or both springs are also within the scope of the invention.

Figure 3:
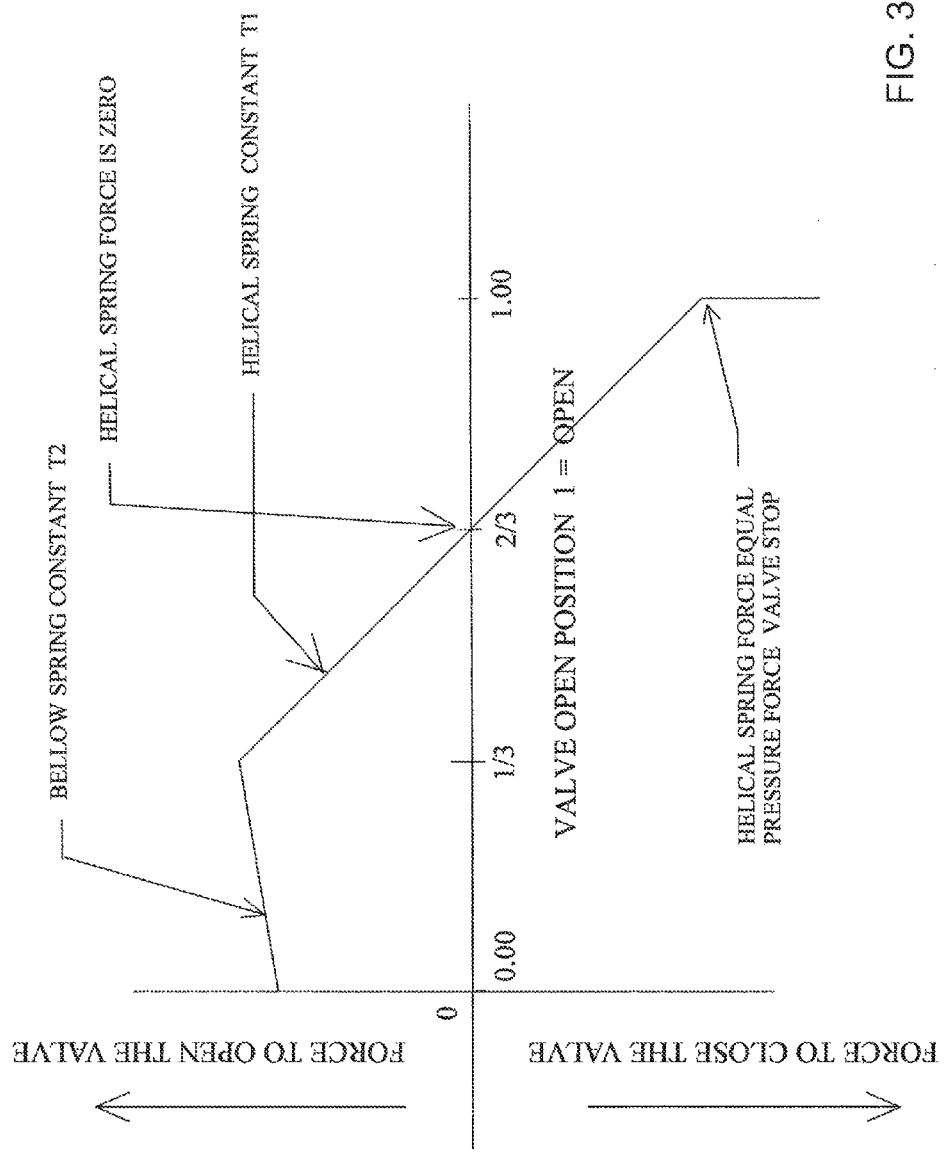
FIG. 3 illustrates a schematic graph illustrating the spring force of valve springs with respect to the axial opening position of the valve.

As noted above, actuation of the valve can be controlled significantly by the force provided by the helical springs 1, 2. The helical springs 1, 2 can be configured in some embodiments to be non-linear such that at about a predetermined fraction X of total axial valve motion dimension (e.g., ⅓ in some embodiments, or about 10%, 15%, 20%, 25%, 30%, 35%, 40%, 45%, 50% in some embodiments) the net force on the valve assembly is zero or substantially zero, as illustrated schematically in the schematic graph of FIG. 3 showing spring forces with respect to the valve opening position. This position does not change substantially in some embodiments even with varying blood pressure due to the non-linear nature of the helical springs 1, 2. Whatever additional change is necessary to close the valve can be compensated by elongation of the bellows spring 4. The bellows spring 4 in some embodiments can have a spring constant that is less than that of the helical springs 1, 2. In some embodiments, the bellows spring 4 has a spring constant that is about, or less than about 90%, 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2%, 1%, or less with respect to the spring constants of the helical springs 1, 2. In some embodiments, the bellows spring 4, has a spring constant that is between about 30% and about 70%, or about 50% with respect to the spring constant of the helical springs 1, 2.

Still referring to FIG. 3, when the valve reaches 1–X (e.g., ⅔ in some embodiments; 50%, 55%, 60%, 65%, 70%, 75%, 80%, 85%, 90%, or more in some embodiments) of the total axial valve motion dimension, the helical spring force will equal the pressure force, and the helical springs 1, 2, and movable valve plate 3 will stop moving. The bellows spring 4 and movable valve plate 5 will continue to move upstream by virtue of the spring constant of the bellows spring 4, which will axially extend the bellows spring 4 and movable valve plate 5 until the movable valve plate 5 contacts the fixed bottom valve ring 7, thereby closing the valve. This can be advantageous in some embodiments as the helical spring force is preset and acts to move the movable valve plate 5 only part of the way (e.g., about ⅔ of the way, or other dimension as discussed elsewhere herein) axially toward the fixed bottom valve ring 7. The spring force of the bellows spring 4 then essentially takes over to move the movable valve plate 5 the remainder of the distance (e.g., ⅓ of the axial valve dimension) to contact the fixed bottom valve ring 7 to close the valve in a gentle manner with reduced force, as the spring constant of the bellows spring 4 can be less than that of the helical springs 1, 2 as noted above. As such controlling the spring constants of the helical springs 1, 2, and the bellows spring 4 can allow for the valve 100 to move from a closed to a fully open, and vice versa position with reduced pressure forces acting on the valve components, potentially prolonging the life of the valve 100 significantly. The relatively small surface contact area of the movable valve plate 5 with respect to the fixed bottom valve ring 7 can also reduce the area of pressure force to the valve. This reduced opening and closure force can be especially significant, for example, for a mitral valve replacement when the left ventricle is contracted. The valve closing force is typically relatively high for conventional valves, which can be reduced by the helical spring force.

Figure 4:
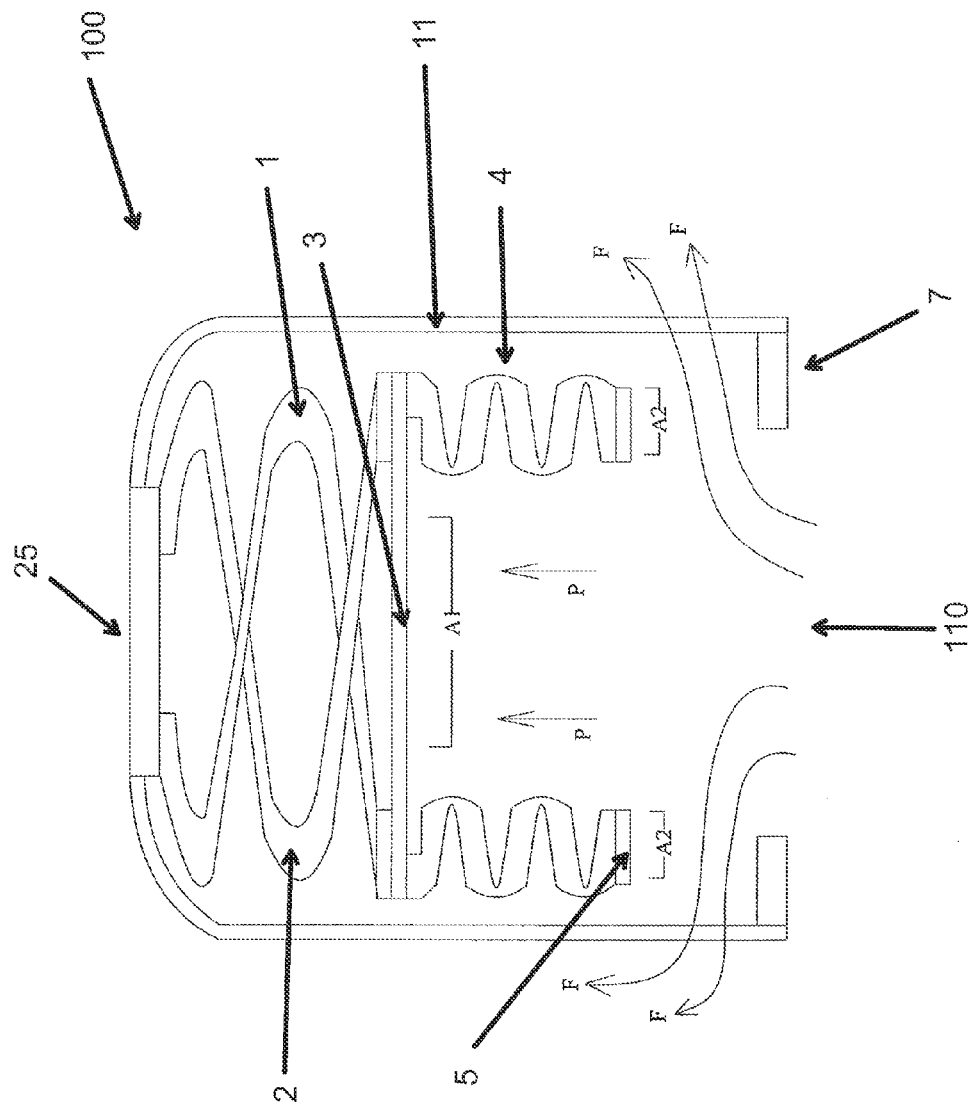
FIG. 4 illustrates a sectional schematic view of an artificial heart valve in an open position, according to some embodiments of the invention.
Figure 5:
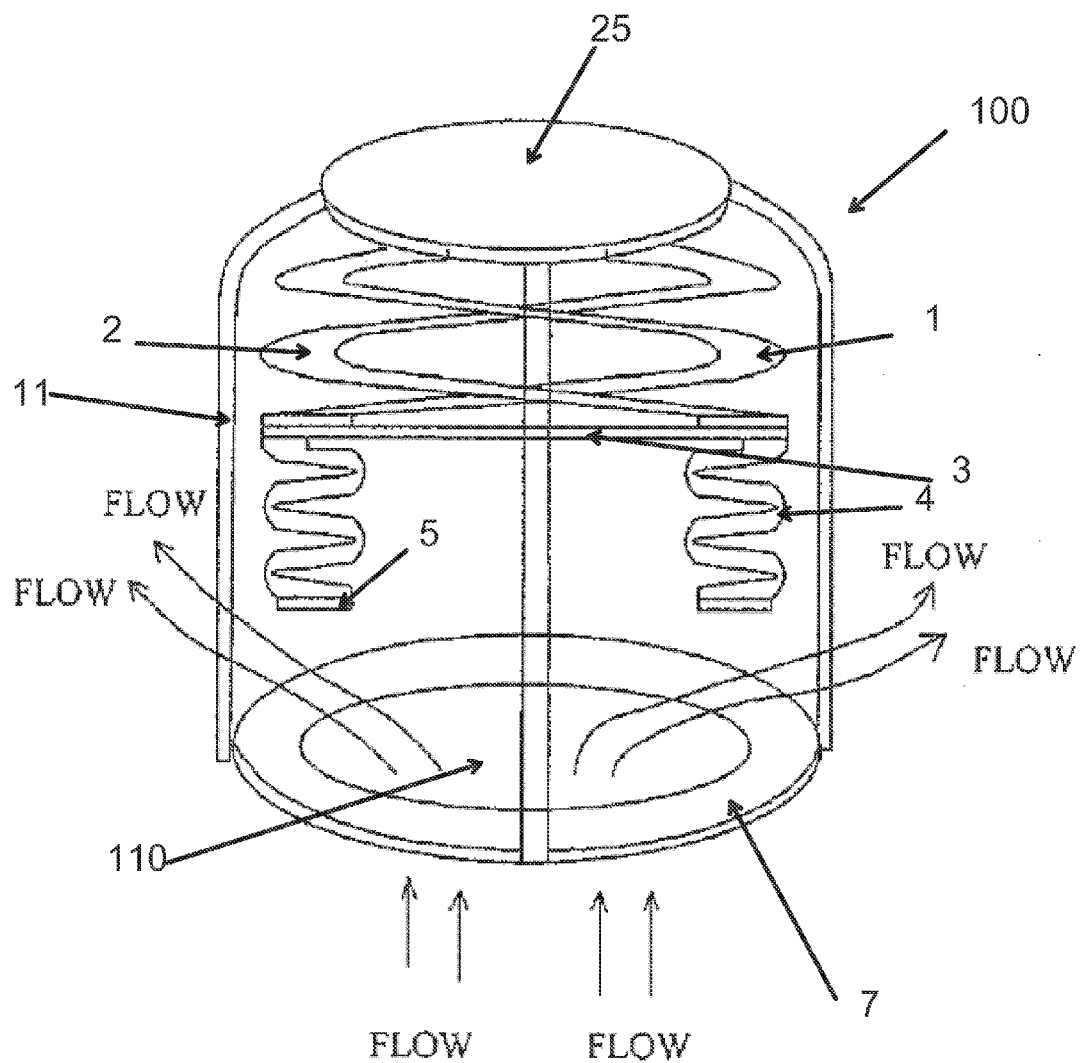
FIG. 5 is a perspective view of the valve illustrated in FIG. 4.

FIG. 4 illustrates the valve 100 in an open position, illustrating blood flow in direction of arrows F through the valve 100, and the direction of pressure forces P to move the valve 100 to a fully open position. The bellows spring 4 attached to the moving valve plate 5 helps to redistribute/cushion pressure forces on the valve 100 caused by valve closing. When the valve 100 is open, the force pushing on the valve in some embodiments can be $(A1+A2)*P$ wherein A1 is the surface area of a surface of the movable spring plate 3 and A2 is the surface area of the movable valve plate 5. When the valve 100 is closed, the force on the valve 100 is about $(\frac{1}{2})*A2*P+(T2*D2)$, and the force per unit area becomes small. The helical springs 1, 2, hold the moving plate. The force on the valve 100 is reduced to about $0.5 A2*P$, which can be less than about 50%, 45%, 40%, 35%, 30%, 25%, 20%, 15%, 10%, or less relative to the force on the valve 100 when the valve 100 is open. FIG. 5 illustrates a perspective view of the valve 100 in an open position illustrated in FIG. 4.

In some embodiments, the valve can be configured to have any number of the following advantageous features. For example, the valve can advantageously have a long life expectancy as there are no parts that slide or rotate against each other. The movement of the valve can be controllable by the helical spring(s) configured to move a preset distance, the distance by itself insufficient to close the valve. The valve contact area can be relatively large, to reduce or prevent red blood cell hemolysis from coaption or turbulent blood flow. The discrete bellows spring can also reduce pressure on the valve, in combination with the aforementioned preset helical springs, and increase the tolerance of operating parts of the valve. The valve contact force can be reduced by the helical spring force as mentioned above. The helical spring force can help commence valve opening; stop valve movement by virtue of the helical spring force, resulting in a no-contact stop; and commence valve closing without necessarily contributing a force at the moment of valve closure (while slowing down/reducing the closing force by virtue of the discrete bellows spring. The motion of the valve can be gentle, and the valve can include no parts that slide against each other. The valve life can be long, such as 5, 10, 15, 20, 25, 30, 35, 40, 45, 50, 60, 70, 80, 90, 100, or more years. The valve can be made of all metallic parts for reduced wear.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "attaching an artificial valve to a native valve annulus" includes "instructing the attaching of an artificial valve to a native valve annulus." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. An artificial heart valve, comprising:
   a moveable valve ring that moves to a flat valve plate to form a seal valve;
   a flat contact area between the moveable valve ring and the flat valve plate, to minimize the force per unit area of contact between the moveable valve ring and the flat valve plate; and
   a bellows spring operably attached to the moveable valve ring, wherein the bellows spring is operably hung to a helical spring assembly,
   wherein an end of the helical spring assembly is operably attached to a cage housing,
   wherein the bellows spring has a first spring constant and the helical spring assembly has a second spring constant, the first spring constant and the second spring constant configured to assist in opening and closing of the valve, minimizing pressure and keeping movement gentle,
   wherein the bellows spring and the helical spring assembly are configured to isolate pressure on the valve, and substantially prevent high pressure forces from acting on the valve,
   wherein the bellows spring is suspended on the helical spring assembly, reducing the pressure on the valve, and wherein the valve is configured such that a flat valve plate force is effected substantially only by an area of the moveable valve ring that contacts the flat valve plate to seal the valve, minimizing the effect of blood pressure on valve pressure.

2. The artificial heart valve of claim 1, wherein the moveable valve ring is configured to not move radially or slide to lengthen the lifespan of the valve.

3. The artificial heart valve of claim 2, wherein the valve is configured such that the impact force upon closure of the valve is minimized, and movement of the bellows spring and the helical spring assembly are programmed to control the valve.

4. The artificial heart valve of claim 3, wherein the valve comprises a metal or plastic material.

5. An artificial heart valve, comprising:
a movable valve plate configured to reversibly contact a proximal valve ring to create a seal and close the valve; wherein at least some stress forces on the valve are alleviated via at least one helical spring operably attached to a bellows spring, the bellows spring operably attached to the movable valve plate, wherein the bellows spring has a pre-selected spring constant sufficient that the movable valve plate contacts the proximal valve ring substantially entirely by virtue of the spring force of the bellows spring, reducing the impact force on the valve.

6. The artificial heart valve of claim 5, wherein the bellows spring pre-selected spring constant is sufficient to prevent a sudden stop force on the movable valve plate or the proximal valve ring.

7. The artificial heart valve of claim 5, wherein the proximal valve ring has a first surface having a surface area and the movable valve plate has a second surface having a surface area, wherein less than the entire surface area of the first surface and the second surface reversibly contact each other to create the seal to close the valve in order to reduce the pressure force on the valve.

8. The artificial heart valve of claim 5, configured to reduce hemolysis of red blood cells flowing through the valve by virtue of at least the large contact area and low impact force on the valve.

9. The artificial heart valve of claim 5, configured such that no valve component is configured to move in a direction other than coaxial with respect to the longitudinal axis of the valve.

10. The artificial heart valve of claim 5, configured to have a long life expectancy within a patient of at least 25 years.

11. An artificial heart valve, comprising:
a valve housing comprising a distal plate and a proximal valve ring operably connected by a plurality of struts;
one or more helical springs having a proximal end and a distal end; and
a bellows spring having a proximal end, enclosed area, and a distal end, the distal end of the bellows spring operably attached to a first surface of a moving spring plate positioned axially in between the one or more helical springs and the bellows spring, the proximal end of the helical spring operably attached to a second surface of the moving spring plate; and
a movable valve plate operably attached to the proximal end of the bellows spring,
wherein the movable valve plate is configured to reversibly contact the proximal valve ring to create a seal and close the valve.

12. The artificial heart valve of claim 11, comprising a plurality of intertwined helical springs.

13. The artificial heart valve of claim 11, wherein one or more of the helical springs, bellows spring, movable valve plate, and the movable spring plate are configured for axial movement with respect to the valve housing, but not radial movement with respect to the valve housing.

14. The artificial heart valve of claim 11, wherein the one or more helical springs are nonlinear.

15. The artificial heart valve of claim 11, wherein the one or more helical springs has a first spring constant and the bellows spring has a second spring constant, wherein the first spring constant is greater than the second spring constant.

16. The artificial heart valve of claim 11, wherein the first spring constant is at least about 25% greater than the second spring constant.

17. The artificial heart valve of claim 11, wherein the first spring constant is at least 50% greater than the second spring constant.

18. The artificial heart valve of claim 11, wherein the valve comprises biocompatible titanium or an alloy thereof.

19. The artificial heart valve of claim 11, wherein the entire valve is made of biocompatible titanium or an alloy thereof.

20. The artificial heart valve of claim 11, wherein the force at the moment of valve closing is provided by the bellows spring but not the one or more helical springs.

21. The artificial heart valve of claim 11, configured to minimize hemolysis of red blood cells upon coaption of the valve.

22. The artificial heart valve of claim 11, wherein the helical spring force assists in opening the valve to a fully open position, and commencing valve closing without providing a force at the moment of valve closure.

* * * * *